United States Patent
Shikinami et al.

(10) Patent No.: US 6,632,503 B1
(45) Date of Patent: Oct. 14, 2003

(54) BIODEGRADABLE AND BIOABSORBABLE IMPLANT MATERIAL AND METHOD FOR ADJUSTING SHAPE THEREOF

(75) Inventors: Yasuo Shikinami, Osaka (JP); Masaki Okuno, Osaka (JP); Hiroshi Morii, Osaka (JP)

(73) Assignee: Takiron Co., Ltd., Osaka (JP)

( * ) Notice: Subject to any disclaimer, the term of this patent is extended or adjusted under 35 U.S.C. 154(b) by 0 days.

(21) Appl. No.: 09/395,349

(22) Filed: Sep. 14, 1999

(30) Foreign Application Priority Data

Sep. 14, 1998 (JP) .......................... 10-279389

(51) Int. Cl.⁷ ................................ B32B 3/10
(52) U.S. Cl. ..................... 428/131; 606/60; 606/70; 606/76; 606/77
(58) Field of Search .................. 428/131; 606/60, 606/61, 69, 70, 71, 72, 73, 75, 76, 77

(56) References Cited

U.S. PATENT DOCUMENTS 6,221,075 B1 * 4/2001 Tormala et al. ............... 606/77

FOREIGN PATENT DOCUMENTS

| EP | 0 795 336 A1 | 9/1997 |
|----|--------------|--------|
| WO | WO 90/07304 | 7/1990 |
| WO | WO 97/11725 A1 | 4/1997 |
| WO | WO 99/44529 | 9/1999 |

OTHER PUBLICATIONS

European Search Report (No Date).
Communication from European Patent Office.

* cited by examiner

Primary Examiner—Paul Thibodeau
Assistant Examiner—Christopher Paulraj
(74) Attorney, Agent, or Firm—Sughrue Mion, PLLC

(57) ABSTRACT

This invention provides a biodegradable and bioabsorbable implant material having a high mechanical strength wherein its shape after deformation within ordinary temperature range can be fixed and maintained so that its shape can be easily adjusted at the site of operation, and it has substantially no anisotropy in view of strength so that it does not cause whitening, breakage and sharp decrease in strength when its bending deformation is repeated in any direction and it has toughness. Particularly, it provides an implant material which comprises a biodegradable and bioabsorbable crystalline polymer that has a crystallinity of 5% or more, can effect deformation such as bending or twisting within ordinary temperature range and has a shape-keeping ability to fix and maintain the shape after deformation as such, wherein molecular chains, domains of molecular chain assembly or crystals of the polymer are oriented along a large number of reference axes having different axial directions, or clusters having these reference axes having different orientation are assembled in a large number.

10 Claims, 12 Drawing Sheets

*FIG. 3A* *FIG. 3B*
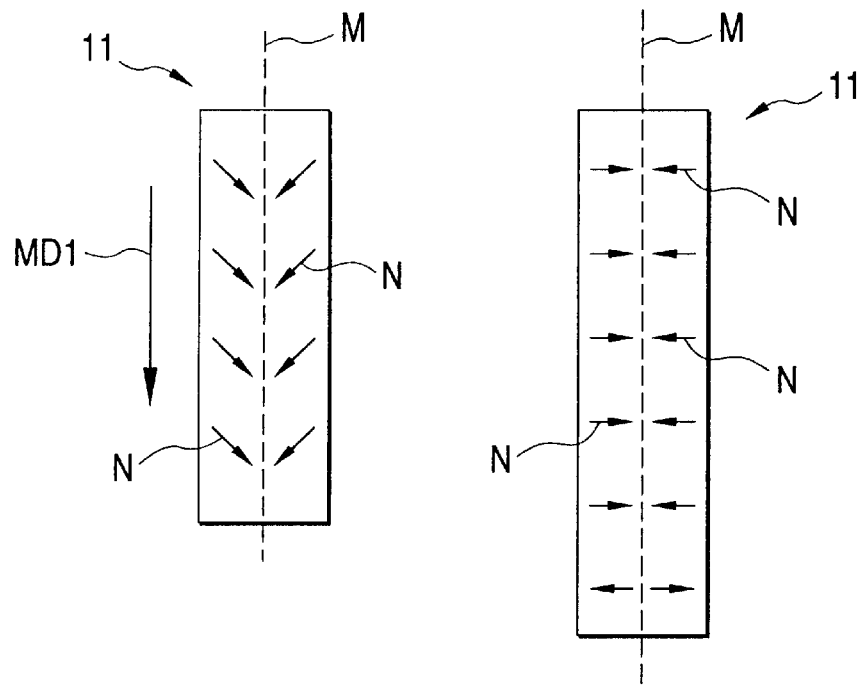
*FIG. 4*
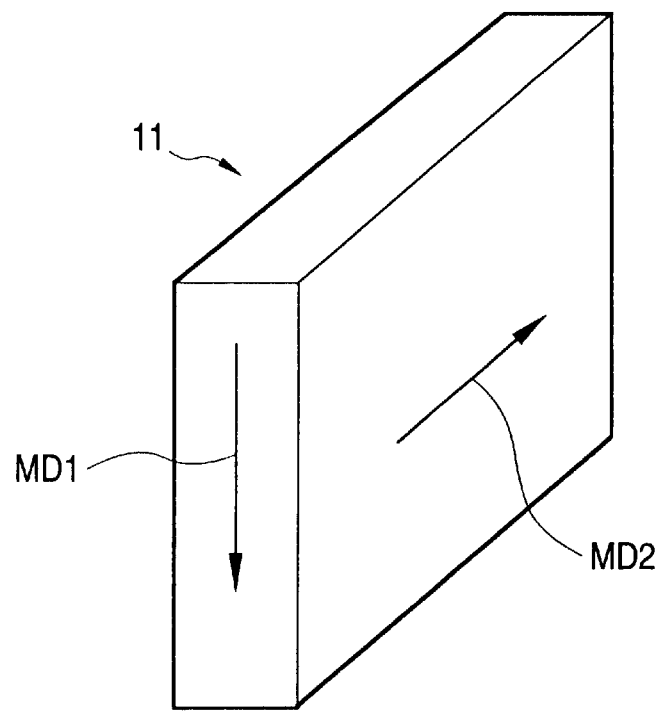

BIODEGRADABLE AND BIOABSORBABLE IMPLANT MATERIAL AND METHOD FOR ADJUSTING SHAPE THEREOF

FIELD OF THE INVENTION

This invention relates to a convenient biodegradable and bioabsorbable implant material which is a biomaterial having high mechanical strength and less mechanical anisotropy, can easily be deformed by bending and/or twisting within ordinary temperature range, has an ability to fix and keep its shape after the deformation as such and can be adjusted into a shape adapted to the surface shape of the region to be applied in the living body in using as such devices of plates, pins and wires.

BACKGROUND OF THE INVENTION

There are various types of implant materials to be implanted in the living body; for example, devices such as plates, pins and wires made of metals or ceramics are frequently used in the case of osteosynthesis.

However, being extensively high in elastic modulus in comparison with natural bones, these implant materials have a problem of reducing strength of peripheral bones due to a stress reducing phenomenon after healing and are excessive shielding strength. Particularly, in the case of implant materials made of metals, they have problems in that elution of metal ions may exert bad influences upon the living body, sometimes causing a danger of generating carcinogenicity and that, when they are left in the living body for a prolonged period of time after completion of their role such as osteosynthesis, they inhibit natural growth of bones so that it is suitable to carry out re-operation to take out the implant devices from the living body at an early stage after healing such as of bone fracture.

Accordingly, studies have been carried out on biodegradable and bioabsorbable implant materials, and devices for osteosynthesis which are molded with a polyglycolic, a polylactic acid or a copolymer thereof have been developed. Such materials for osteosynthesis, particularly the materials for osteosynthesis made of a polylactic acid, are biocompatible because of their good affinity for the alive body and have a favorable property in that they are gradually hydrolyzed in the living body by the contact with body fluids and finally absorbed by the living body, so that they are frequently used in recent years. In addition, it is not necessary to remove them by re-operation, which is different from the case of the implant devices made of metals.

However, a mini-plate material, etc. made of titanium for use in oral and maxillofacial surgery and brain surgery has an advantage in that it can be used by freely deforming its shape during operation to exert sufficient fixing ability by closely adjusting it to the shape of bone to be treated. Accordingly, in many cases, the same characteristics, i.e., bend-deforming the devices to conform to the shape of the bone upon use, is also in demand for implant devices such as plates for osteosynthesis molded with polylactic acid. As a matter of course, a material prepared to have a flat type shape may be used as such in some cases. Such a plate can be used in the scene of operation by thermoforming it at a temperature of approximately from 60 to 80° C. to adjust it to the shape of the surface of bone to be treated. Although it is a practical method which uses conventional knowledge on the thermoorming of plastics, it requires complex handling.

In general, a molding of polylactic acid having a flat shape such as plate can be easily deformed by bending at ordinary temperature when the thickness is thin. However, when its bending deformation is carried out at an ordinary temperature which is lower than its glass transition point (Tg), whitening occurs in the bending-deformed part portion due to change of the morphology and its strength is reduced, thus causing a problem in that it cannot be used as a plate for osteosynthesis. Thus, in reality, its bending deformation has to be made by heating and softening it as described in the foregoing.

In the polylactic acid implant materials so far developed, uniaxial drawing is carried out by various methods for the purpose of increasing strength, and the polymer molecules and crystals are oriented along the drawing direction by this treatment. At the same time, the polymer becomes fibers when the draw ratio is increased. By the use of their assembled form, a device for osteosynthesis having markedly increased strength of mechanical direction (MD) can be prepared. However, since an implant device in which the polymer molecules are uniaxially oriented in this manner has considerably large anisotropy. Accordingly, the bent part whitens and is easily broken when it is bending-deformed at ordinary temperature by merely a small number of times but to a direction falling at right angle with the orientation direction. It also causes a problem in that it is easily broken when twisted in the orientation direction around the sequence of fibers. Accordingly, it is also difficult to carry out torsional deformation.

In addition, there are other unsolved problems in that, since implant materials solely made of a polylactic acid have no ability to bond to bones, bones cannot be fixed securely because of a possibility to cause loosening after its application to bones. In addition, since they have no bone conductivity, their replacement by bones after degradation and absorption cannot be easily completed.

The present invention was accomplished by taking the aforementioned problems into consideration. The object of the present invention is to provide a biodegradable and bioabsorbable implant devices which have basically large mechanical strength, can be deformed by bending or twisting within ordinary temperature range and can fix and keep the resulting shape as such, has substantially no anisotropy of strength, can be subjected to repeated deformation of exceeding 20 times (can withstand repeated deformation of more than several hundred times in the case of a wire having a circular section) because of its ability of not easily causing whitening and reduced strength by its deformation in any direction partially due to the change of morphology, and also can give a property to bond to bones within a short period of time as well as a bone conductivity.

SUMMARY OF THE INVENTION

In order to achieve the aforementioned object, the biodegradable and bioabsorbable implant material according to the first embodiment of the present invention is characterized in that it comprises a biodegradable and bioabsorbable crystalline polymer capable of effecting deformation such as bending or twisting within ordinary temperature range and having a shape-keeping ability to fix and maintain the shape after deformation as such, wherein molecular chains, domains of molecular chain assembly or crystals of the biodegradable and bioabsorbable polymer are oriented along a large number of reference axes having different axial directions, or clusters having these reference axes having different orientation are assembled in a large number.

The term "orientation along a large number of reference axes having different axial directions" or "assembly of clusters having reference axes of different orientation" means a multi-axial orientation or an oriented form as the assembly of multi-axially oriented clusters, so that its meaning is completely different from that of no orientation which means no oriented form (so-called randomly oriented form having no orientation treatment). Also, the term "ordinary temperature range" means a temperature range of from 0° C. or more to less than 50° C.

Also, the biodegradable and bioabsorbable implant material according to the second embodiment of the present invention is the implant material as set forth in the first embodiment, wherein it is obtained by forging a billet comprising a biodegradable and bioabsorbable crystalline polymer at a low temperature between Tg and less than Tm (Tg: glass transition temperature; Tm: melting temperature) and then forging it at the temperature by changing its mechanical direction (MD) (which may be carried out a plurality of times), and the biodegradable and bioabsorbable implant material according to third embodiment of the present invention uses a crystalline polylactic acid as the biodegradable and bioabsorbable crystalline polymer. Also, the biodegradable and bioabsorbable implant material according to the fourth embodiment of the present invention is an implant device for osteosynthesis use which is formed into a flat heteromorphic shape such as a sheet, a plate, a plate having screw-inserting hole(s), a washer, a button, a mesh or a ribbon, the biodegradable and bioabsorbable implant material according to the fifth embodiment of the present invention is an implant device which is formed into a cylindrical shape such as a wire, a cable prepared by making up thin wires into a bundle and twisting the bundle, a rod or a pin, and the biodegradable and bioabsorbable implant material according to the sixth embodiment of the present invention is characterized in that it further contains a bioceramics powder. In this connection, the "billet" of the second embodiment of the present invention is not limited to a round bar and its shape is not limited, so that it may be a polygonal prism having different number of angles. The seventh embodiment of the present invention is a biodegradable and bioabsorbable implant material wherein the state of orientation of molecular chains, domains of molecular chain assembly or crystals of the biodegradable and bioabsorbable polymer partially changes by the deformation within ordinary temperature.

In addition, the shape-adjusting method of eight embodiment of the present invention is characterized in that the biodegradable and bioabsorbable implant material as set forth in any one of the aforementioned first to seventh embodiments of the present invention is subjected to bending deformation and/or torsional deformation within ordinary temperature range and then the shape after deformation is fixed and kept as such.

Other objects and advantages of the present invention will be made apparent as the description progresses.

BRIEF DESCRIPTION OF THE DRAWINGS

Each of FIGS. 1A to 1F is an illustration showing plan view of a biodegradable and bioabsorbable implant device for osteosynthesis use, in which 1A is a straight type material, 1B is an L type, 1C is a T type, 1D is a Y type, 1E is a C type and 1F is a straight type having no "necking", and 1G in the drawing is an illustration showing plan view of a ribbon-shaped biodegradable and bioabsorbable implant material for orthopaedic surgery use. In the drawing, 1 is a screw insertion hole.

FIG. 3A and FIG. 3B show the crystalline orientation state of the molding forged one time. FIG. 3A is a side view and FIG. 3B is a plan view.

FIG. 4 is a drawing showing the mechanical directions (MD) of the forged molding.

FIG. 12A is an X ray photograph when the incident angle of the X ray was parallel to the mechanical direction MD1. FIG. 12B is an X ray photograph when the incident angle of the X ray was right to the mechanical direction MD1.

FIG. 13A is an X ray photograph when the incident angle of the X ray was parallel to the mechanical direction MD2. FIG. 13B is an X ray photograph when the incident angle of the X ray was right to the mechanical direction MD2.

DETAILED DESCRIPTION OF THE INVENTION

Figure 1A:
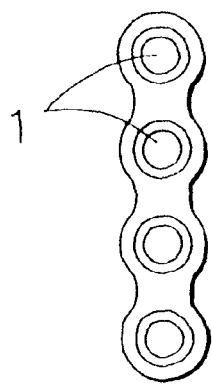
Figure 1B:
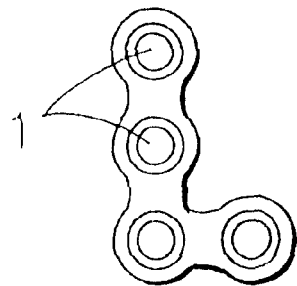
Figure 1C:
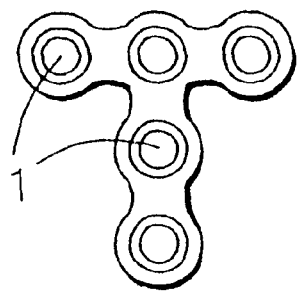
Figure 1D:
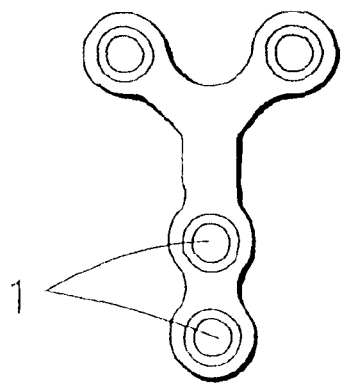
Figure 1E:
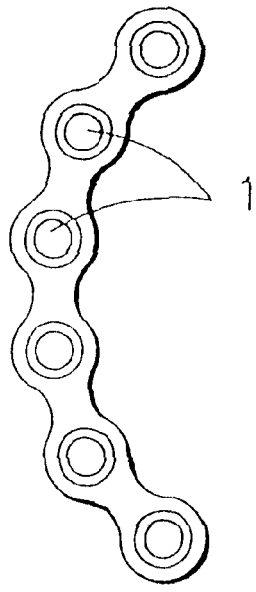
Figure 1F:
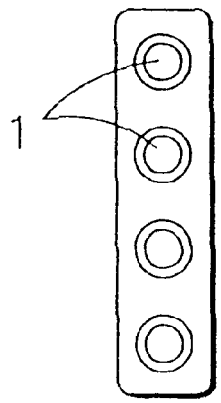
Figure 1G:
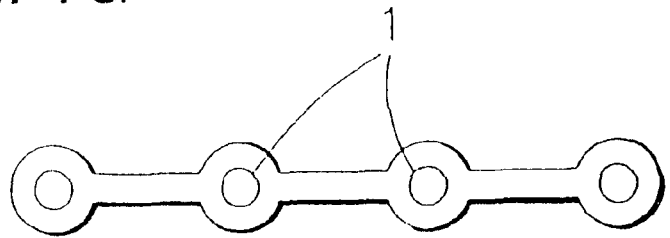

A crystalline plastic having a glass transition point (Tg) of lower than the usual room temperature (from 25 to 30° C.) generally has a morphological phase structure comprising a crystal phase and a rubber phase at room temperature. Because of the presence of rubber layer, the shape after its bending within ordinary temperature range can hardly be kept and fixed and is restored by its elasticity. Polyethylene (Tg: −20° C.) and polypropylene (Tg: −10° C.) are its familiar examples, and when they are deformed within the ordinary temperature range defined by the present invention and then the external force is removed, they are restored to the original shape or a shape close to the original shape by the rubber elasticity.

On the contrary, a crystalline polylactic acid or the like as a typical example of the biodegradable and bioabsorbable polymer to be used in the present invention has a glass transition point (Tg) of higher than the ordinary temperature range (60 to 65° C.), shows a phase structure mainly comprising a crystal phase and a glass phase within the ordinary temperature range and contains substantially no rubber phase even when the crystallinity is at least 5% or more, so that its shape after bending deformation within the ordinary temperature range can be kept and fixed as such. The aforementioned polymer such as polylactic acid is an assembled body in view of material morphology in which molecular chains, domains of molecular chain assembly or crystals of the polymer are oriented along a large number of reference axes having randomly different axial directions (that is, expression of three-dimensional orientation of a plurality of axial directions is found statistically) or clusters having reference axes having randomly different orientation are assembled in a large number, so that such a deformation property capable of keeping and fixing its shape after bending or twisting treatment is expressed by the generation of mutual "shearing" between surfaces of these assembled masses. Accordingly, it is considered that, when deformation is effected in a certain direction, an assembled body having a crystal phase oriented along that direction is formed, so that it acts as a back up of strength in the deformation direction and, therefore, durability of repeated deformation is generated even against various deformation directions and twisting.

Among the aforementioned polylactic acids, a crystalline poly-L-lactic acid as L-isomer homopolymer and an crystalline poly-D-lactic acid as a D-isomer homopolymer are basically composed of a crystal phase and a glass phase, but a poly-D/L-lactic acid as a copolymer of D-isomer and L-isomer keeps back a crystal phase when the molar ratio of any one of the D-isomer and L-isomer exceeds 80% (88% according to a certain literature) and, when the ratio is 80% or less, the crystal phase mostly disappears and the polymer becomes basically glassy. In consequence, when a ploy-D/L-lactic acid is used, it is desirable to use a copolymer having a D-isomer/L-isomer molar ratio of approximately 80/20 or more or approximately 20/80 or less and a remaining crystallinity of approximately 5% or more. The Tg value of such a poly-D/L-lactic acid having a crystallinity of 5% or more and the Tg values of the aforementioned poly-L-lactic acid poly-D-lactic acid are higher than 50° C. which is the upper limit of the "ordinary temperature range" of the present invention. That is, the present invention relates to a material having a characteristics that it is freely deformed and fixed at a temperature which is equal to or less than its Tg value and also relates to a deformation method thereof. The ordinary temperature range effective for deformation and fixing is employed as a particular characteristic of the present invention. When a billet of such a crystalline polymer is forged at low temperature between Tg and less than Tm and again forged once or a plurality of times at the temperature by changing its mechanical direction such as the case of the second embodiment of the present invention, an implant device having less anisotropy in view of strength and markedly higher strength than that before the forging is obtained. It is considered that such an effect is obtained due to formation of the orientation of molecular chain assembly domains and the orientation of crystals based on the intermolecular and intramolecular mutual actions generated by the aforementioned particular temperature processing of the present invention. In addition, packing density of the material of a molding is considerably increased without having directional property by the pressure added toward the direction of the central part of a billet at the time of its forging treatment.

In order to orient molecular chains, domains of molecular chain assembly or crystals of an implant material forged in the aforementioned manner along a large number of reference axes in which axial directions are arranged in many directions, the forging is effected at a temperature of approximately from 70 to 130° C. which is considerably higher than the ordinary temperature but fairly lower than the usual thermoforming temperature. Therefore, when the implant material is deformed within the ordinary temperature range and embedded in the living body, the crystal phase which does not melt at ordinary temperature behaves as a back up structure phase at the time of deformation (the temperature Tm at which the crystal phase melts is about 180° C. which is fairly high) Accordingly, the shape after deformation is maintained as such and does not remember to its original shape by the body temperature. In other words, restoration of the original shape through disappearance of the orientation requires a temperature rising at least to a level of the forging-treated temperature or more, but the forging temperature is within the range of from 70 to 130° C., which is fairly higher than the body temperature as described in the above, so that it does not remember to its original shape.

On the other hand, when bending deformation is carried out within the ordinary temperature range with respect to a non-oriented material in which molecular chains, domains of molecular chain assembly or crystals do not have the aforementioned orientation modes or a material having an orientation only in a single direction (uniaxial direction), a large "shear" is easily formed in the deformed part and produces a morphological part a configuration which is different from the peripheral non-deformed parts, thus resulting in the formation of microscopic faults, so that whitening occurs sometimes which easily entails cutting failure of the material. However, in the case of a material in which molecular chains, domains of molecular chain assembly or crystals are multi-axially oriented, or multi-axially oriented clusters are assembled, as in the case of the implant material of the present invention, it does not cause whitening when bending deformation is carried out in any direction over a large number of times in comparison with a non-oriented or single direction-oriented material so that cutting failure of the material does not occur. In addition, reduction of strength (deterioration) at that time is very little and about 80% or more of the initial bending strength is maintained after repeated bending deformation, as is evident from the test data which will be described later. Such a feature is far superior to that of a titanium plate which has ductility and toughness and can easily be deformed at the site of surgical operation. In consequence, when the implant material of the present invention is subjected to bending deformation and/or torsional deformation within ordinary temperature range and the shape after deformation is fixed and kept as such, as in the case of the shape-adjusting method of the seventh embodiment of the present invention, decisive reduction of strength does not occur so that the implant device can be embedded in the living body by easily adjusting its shape during the operation. Such an excellent mechanical property cannot at all be obtained by the conventional biodegradable and bioabsorbable implant material without orientation or with uniaxial orientation. This is also an essential characteristic when a heteromorphic plate which will be shown later by drawings is used by its deformation.

The aforementioned biodegradable and bioabsorbable implant material is formed, for example, into an implant device for osteosynthesis use, having a flat heteromorphic shape such as a sheet, a plate, a plate having screw-inserting hole(s), a washer, a button, a mesh or a ribbon, as in the case of fourth embodiment of the present invention, and used for the bone healing at the site of operation by adjusting its shape to the irregular surface shape of bones through its bending deformation or torsional deformation within the ordinary temperature range. Such an implant material for osteosynthesis use may be a material in which a flat plate is slightly bent or twisted in advance to a predetermined shape. As in the case of the fifth embodiment of the present invention, it is also formed into a round or square cylindrical shape such as a wire, a cable prepared by making up thin wires into a bundle and twisting the bundle, a rod or a pin and used at the site of operation, for example, by twist-deforming it as a wire for bone healing or bend-deforming it in response to the bending degree of bones to be healed.

In that case, when a bioceramics powder is included as in the case of the implant material of the sixth embodiment of the present invention, the bioceramics powder exerts an action to deposit and form calcium phosphate existing in the living body on the surface layer of the implant material, so that the implant device binds to the device bone within a relatively short period of time. In consequence, loosening hardly occurs and the fractured bones can be fixed securely. It also expresses a property to conduct formation of new bone to a lost bone region which is formed when the said implant device is embedded. It is further effective, because the implant material as a whole is absorbed in the living body and finally disappears at a relatively early stage replaced by the biological bone.

Illustrative embodiment of the present invention is described in detail in the following with reference to the drawings.

Each of FIGS. 1A to 1F is an illustration showing plan view of a biodegradable and bioabsorbable implant device for osteosynthesis use, in which 1A is a straight type material, 1B is an L type, 1C is a T type, 1D is a Y type, 1E is a C type and 1F is a straight type having no "necking",and 1G in the drawing is an illustration showing plan view of a ribbon-shaped bone healing and fixing material for plastic surgery use.

Each type of the implant material is formed into a plate shape of approximately from 0.5 to 3.5 mm in thickness having a plurality of screw insertion hole 1, which can be deformed by its bending or twisting within ordinary temperature range (0° C. or more and less than 50° C.) and has a function to fix and keep its shape after deformation. When the thickness is thinner than 0.5 mm, its strength as a plate for osteosynthesis use may become insufficient. When the thickness is larger than 2.0 mm, a prolonged period of time is required until its complete degradation and disappearance of tactile perception (3 years or more) so that it can hardly be used in the field of oral surgery. When the thickness exceeds 3.5 mm, its weight becomes so heavy that it is necessary to avoid its use even in the field of orthopaedic surgery in order to prevent side effects at the time of its degradation and absorption. Also, since a considerably large force is required for its bending deformation or torsional deformation within the ordinary temperature range, free deformation cannot be made easily.

In addition, though not shown in the drawings, it may have a round or square cylindrical shape such as a wire, a cable prepared by twisting the wires, a rod or a pin. A cylindrical material having, for example, a diameter of from 0.5 to 4.0 mm and a length of from 10 to 30 cm is used, which can be bent, twisted or deformed for example for ligation and is applicable to materials for osteosynthesis use (e.g., pins, wires and the like). It also can be formed into a thin band shape such as a sheet-like ribbon, and such a ribbon has a thickness of from 0.2 to 2.0 mm and a length of from 10 to 30 cm and can be bent, twisted or deformed for example for ligation.

Since these implant devices comprise a biodegradable and bioabsorbable crystalline thermoplastic polymer having a glass transition point (Tg) of higher than room temperature, they have a phase structure basically composed of a crystal phase and a glass phase and their crystallinity is 5% or more. However, it is preferable that the upper limit of the crystallinity does not exceed 70%, because a large number of fine pieces of crystals are formed simultaneously with the degradation of the implant materials as their degradation progresses. Since the amount of the thus formed fine pieces of crystals far exceeds the phagocitosing capacity of macrophages, there is a possibility of causing damage upon peripheral cells and thereby generating inflammation. Also, when the crystallinity exceeds 70%, the polymer loses its toughness and flexibility and becomes brittle, so that molding of the material becomes difficult. In consequence, it is desirable that the crystallinity is 70% or less, preferably from 30 to 50%. In addition, the material comprises a multi-axially oriented form in which molecular chains, domains of molecular chain assembly or crystals of the biodegradable and bioabsorbable polymer are oriented along many reference axes having random axial directions, or an assembled mass in which clusters having reference axes of randomly different orientation are assembled in a large number.

In consequence, these implant materials are practical because, as described in the foregoing, they have substantially no mechanical anisotropy, are not easily broken when bending-deformed in any direction within the ordinary temperature range which is different from the case of a non-oriented or single direction-oriented implant material, shows very little reduction of strength (deterioration) by repeated bending and maintains about 80% or more of the initial bending strength after repeated bending deformation of exceeding 20 times, so that the strength is hardly reduced after several times of deformation at ordinary temperature during operation. Also, in the case of a wire having circular section, it is not broken after 800 times of repeated bending at an upward/downward angle of 15° as will be shown later in Example 3. While a kirschner wire is broken by about 400 times of bending, this wire has such a durability that its initial strength can be maintained during 800 times of bending.

The aforementioned implant materials can be produced by preparing a billet from a biodegradable and bioabsorbable crystalline polymer, forging the billet at a low temperature (glass transition temperature or more and less than melting temperature, preferably from 70 to 130° C., more preferably from 90 to 110° C.), further forging at a low temperature by changing its mechanical direction (MD) to make a plate- or rod-shaped multi-axially oriented body or an assembly of oriented clusters, and then cutting it into various flat plate shapes shown in FIGS. 1A to 1G while simultaneously carrying out a perforation processing. A wire can be produced by cutting the forged plate-shaped molding into a prismatic shape and processing the prism by removing its corners so that its section becomes circular.

Figure 2:
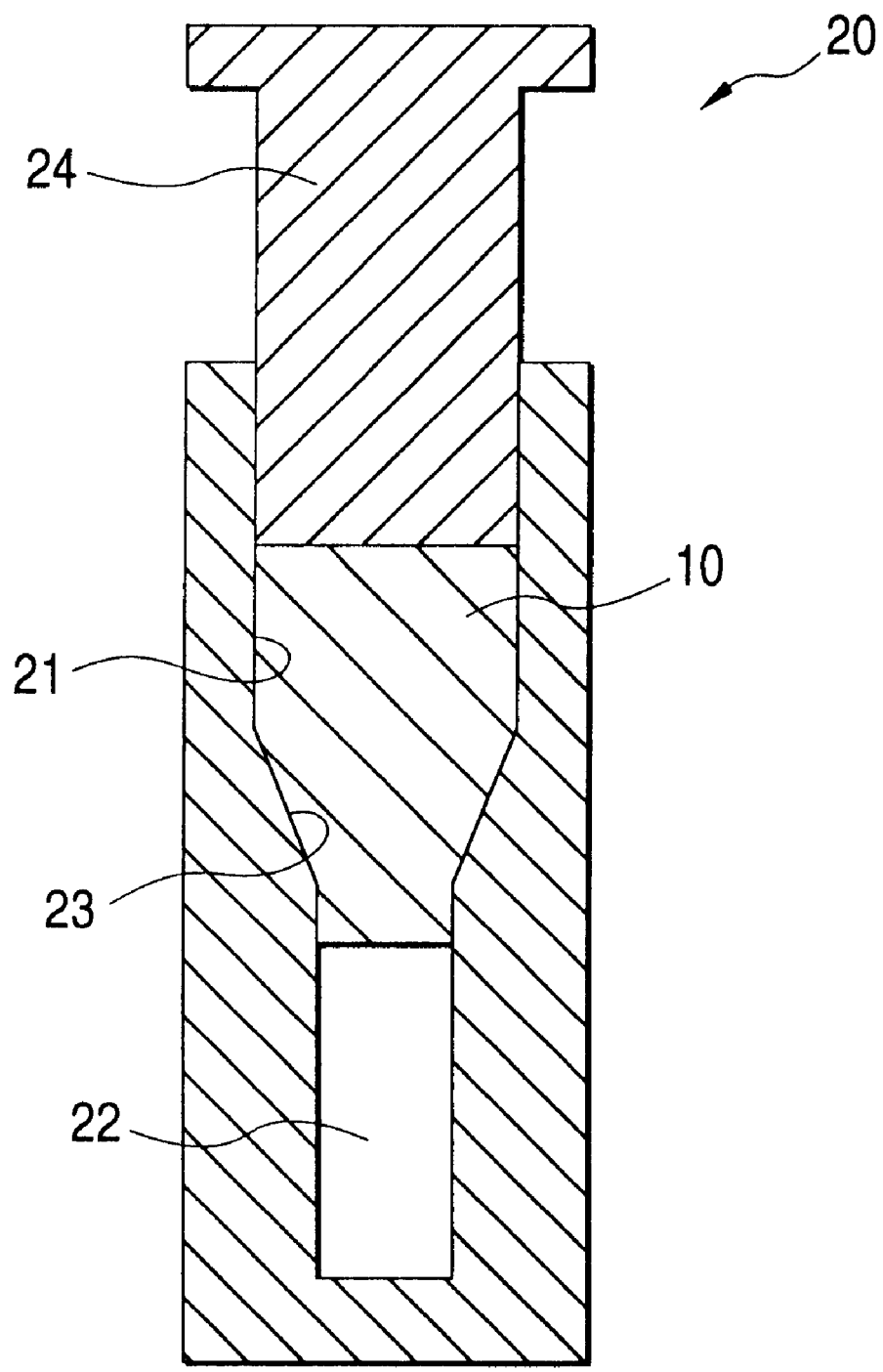
FIG. 2 is a sectional view of a forming mold for producing the biodegradable and bioabsorbable implant material of the present invention.

The implant material of the present invention can be prepared, for example, by the method described below. First, a crystallizable biodegradable and bioabsorbable polymer is made into a billet 10 by the known molding method (e.g., the extrusion molding and the injection molding) at a temperature that is higher than the melting point of the polymer and lower than 220° C. As shown in FIG. 2, the resulting billet 10 is pressed into a small space of the bottom-closed forming mold 20 having a smaller thickness, diameter, etc. than that of the billet 10, while effecting plastic deformation at a low temperature between Tg and less than Tm, to prepare a forged molding block (plate, billet) 11. Then, the resulting forged molding block 11 is pressed into a small space of the bottom-closed forming mold having a smaller thickness, diameter, etc. than that of the forged molding block 11, while effecting plastic deformation at a low temperature between Tg and less than Tm, to prepare the molding 1 of the present invention.

The forming mold 20 shown in FIG. 2 is an example of the forming molding for preparing a plate-shaped forged molding block 11. The forming molding 20 comprises (1) a mold which comprises a part forming a cavity 21 having a rectangular longitudinal section and having a larger lateral sectional area, in which the billet 10 is filled, a bottomed part forming a cavity 22 having a rectangular longitudinal section and having a smaller lateral sectional area (preferably, about ⅔ to ⅙ of the sectional area of the billet), and the tapered part 23 connecting these two and having a trapezoid longitudinal section, wherein these three parts aligned along the same central axis; and (2) a piston 24 which can be inserted into the cavity 21.

The billet 10 filled in the cavity 21 is press-forced into the cavity 22 by continuously or discontinuously applying a pressure, while effecting plastic deformation at a low temperature. The direction of this press-forcing is the mechanical direction MD1. The polymer crystallizes by this forging molding. As shown in FIG. 3A, the crystals of the polymer align in parallel in the directions of a large number of reference axes N that slant toward the axial face M. In this regard, the axial face M is the mechanical core during the molding, i.e., the area containing the continuous points (lines) at which the forces from the both sides of the forming mold are concentrated.

The crystallized forged molding block 11 as it is or after cutting into an appropriate size is then subjected to the second forging molding by changing the mechanical direction MD (i.e., changing the direction of press-forcing). The forming mold used for the second forging molding may be the similar shape with the above-described forming mold 20. That is, the forming molding comprises (1) a mold which comprises a part forming a cavity having a rectangular longitudinal section and having a larger lateral sectional area (having a smaller lateral sectional area than that of the forged molding block 11), in which the forged molding block 11 is filled, a bottomed part forming a cavity having a rectangular longitudinal section and having a smaller lateral sectional area (preferably, about ⅔ to ⅙ of the sectional area of the forged molding block 11), and the tapered part connecting these two and having a trapezoid longitudinal section, wherein these three parts aligned along the same central axis; and (2) a piston which can be inserted into the cavity. The forged molding block 11 is filled into the cavity of the forming molding in a certain direction so that the press-forcing direction of the second forging molding (MD2) becomes different from the press-forcing direction of the first forging molding (MD1). For example, as shown in FIG. 4, MD2 is selected to form an angle of 900 against MD1. Then, the forged molding block 11 is press-forced into the cavity continuously or discontinuously, while effecting plastic deformation at low temperature. By this second forging molding, the crystals of the polymer which have been oriented in parallel along many reference axes are subjected to the rearrangement in the mechanical direction, so that the many reference axes direct toward various directions randomly. As a result, the crystals of the polymer are oriented along a large number of reference axes having different axial directions, or clusters having these reference axes having different orientation are assembled in a large number. The molecular chains and domains of the molecular chains of the polymer are similarly oriented.

In the foregoing, the molding obtained by two times forging moldings was explained. It is possible to conduct further forging molding. The number of total forging moldings is preferably from 2 to 5, more preferably from 2 to 3, because the reference axes along which the crystals orient hardly becomes random and the device obtained can bear to the outer forces such as bending, twisting, etc. in these ranges. Between the forging molding steps, the directions of the press-forcing are changed so as to form an angle in the range of preferably from 10° to 170°, more preferably from 45° to 1350, most preferably 90°.

It is desirable to carry out the forging at such a deformation ratio (sectional area of a billet/sectional area of its forged molding) that fibrillation does not occur, preferably at a deformation ratio of from 1.1 to 3.5.

Crystalline thermoplastic polymers having a crystallinity of 5% or more, which have a glass transition point (Tg) of higher than the upper limit of the ordinary temperature range (50° C.) and are hydrolyzed and absorbed in the living body, are used as the biodegradable and bioabsorbable material polymers, among which polylactic acids having an initial viscosity average molecular weight of from 100,000 to 700,000, preferably from 150,000 to 400,000, namely a poly-L-lactic acid, a poly-D-lactic acid and a poly-D/L-lactic acid (provided that it is a copolymer having a D/L molar ratio of approximately 80/20 or more or approximately 20/80 or less and having a crystallinity of 5% or more) are desirable, and these polymers may be used alone or as a mixture of two or more. A polymer having a crystallinity of from 10 to 70%, preferably from 30 to 50%, is particularly desirable.

A biodegradable and bioabsorbable amorphous polymer having a crystallinity of less than 5%, such as a poly-D/L-lactic acid having a D/L molar ratio of 50/50 and a crystallinity of 0%, shows a certain degree of improvement in strength when it is compressed by forging at a low temperature. However, because of its basically small strength, it is difficult to obtain an implant material which has such a toughness that it does not break by 20 or more times of repeated bending deformation, and such an implant material is apt to return to its original shape when compared with a crystalline polymer, so that the object of the present invention cannot be achieved sufficiently.

The aforementioned biodegradable and bioabsorbable implant device for osteosynthesis is used at the site of operation for connecting fractured bone parts, by bending and/or twisting it within the ordinary temperature range to deform it into such a shape that it can be fitted to the fractured bone parts and then thrusting fixing screws into the biological bone through the screw insertion hole 1. Thus, the implant material of the present invention is markedly convenient, because it does not require a troublesome work of carrying out bending deformation by heating it at about 80° C. and its shape can be adjusted easily by bending or torsional deformation at ordinary temperature and because there is no fear of returning to its original shape in the living body. In addition, the implant material maintains sufficient strength in the living body during a period of from 1 to 6 months, starting from the commencement of hydrolysis on its surface through its contact with the body fluid until healing of the fractured bone parts, but is finely broken thereafter as its hydrolysis progresses and finally absorbed by the living body and completely disappears. In consequence, it is not necessary to take out the material from the living body by re-operation which is common in the case of conventional metallic implant materials, so that mental and economical burdens on patients can be alleviated.

It is desirable to include a bioceramics powder in the aforementioned plate-shaped implant material for osteosynthesis use, because the bioceramics powder which is present on the surface layer or appeared on the surface by hydrolysis of the polymer allows calcium phosphate or bone tissue in the living body to deposit on or conduct to the surface layer region of the implant material, so that the implant material can bind to the living bone and fix the fractured bone parts securely within a relatively short period of time.

Examples of the bioceramics powder to be used include powders of surface-bioactive sintered hydroxyapatite, glass for biological body use of a bioglass or crystallized glass system, biodegradable un-sintered hydroxyapatite (namely, a raw hydroxyapatite which is not treated by sintering or by both sintering or calcination but has a chemical composition similar to that of hydroxyapatite in the living body), dicalcium phosphate, tricalcium phosphate, tetracalcium phosphate, octacalcium phosphate, calcite and diopside, which may be used alone or as a mixed powder of two or more.

It is desirable to use the bioceramics powder at a blending ratio of approximately from 10 to 60% by weight, because the function of bioceramics powder to effect deposition or conduction of calcium phosphate and bone tissue in the living body cannot fully be exerted when the ratio is less than 10% by weight, and the implant material becomes brittle due to reduced toughness when the ratio exceeds 60% by weight.

Examples of the present invention are given below by way of illustration and not by way of limitation.

EXAMPLE 1

Using an extruder, a poly-L-lactic acid (PLLA) having a viscosity average molecular weight of 350,000 was melt-extruded at 190° C. to obtain a prismatic billet of 250,000 in viscosity average molecular weight having a rectangular section of 12 mm in length×50 mm in width.

This billet was forged at 110° C. by press-charging it into the cavity of a forming mold of 7.5 mm in height×32 mm in width×60 mm in length, thereby obtaining a molding. This molding was again subjected to the forging molding by changing its mechanical direction (MD) to obtain a plate-shaped multi-axially orientated compression molding of 60 mm in length×80 mm in width×3 mm in thickness. Crystallinity of this multi-axially orientated compression molding was calculated to be 43% when measured by a differential scanning calorimeter (DSC).

Figure 5:
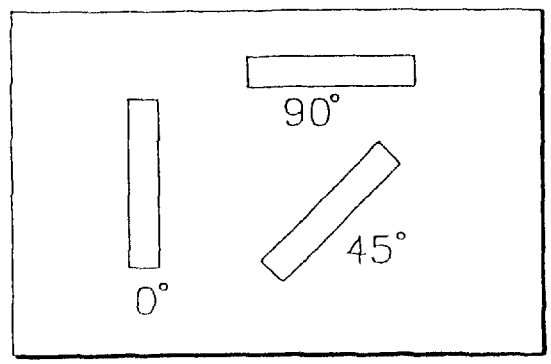
FIG. 5 is an explanatory drawing showing a way of cutting out a rectangular plate from a plate-shaped compression multi-axial orientation molding in Example 1.

As shown in FIG. 5, this multi-axially orientated compression molding was cut out at a direction of 0°, 45° or 90° to prepare a rectangular plate of 30 mm in length×5 mm in width×1.5 mm in thickness. Thereafter, its bending strength was measured using an autograph. The results are shown in Table 1. In this connection, temperature at the time of measurement was 22° C. (room temperature).

Figure 6A:
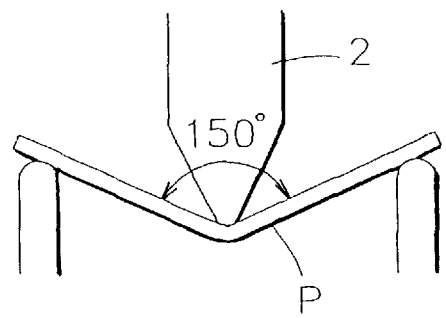
FIGS. 6A and 6B are explanatory drawings showing the repeated bending test carried out in Example 1. In the drawings, 2 is an autograph cross head and P is a plate.
Figure 6B:
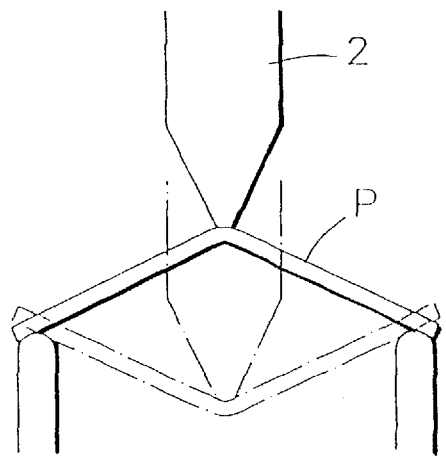

As shown in FIG. 6A, using each of the aforementioned plates cut out in a direction of 0°, 45° or 90°, the plate P was pressed at its central position with a cross head 2 of the autograph until its bending angle became 150°, and the load at that time was measured. Also, as shown in FIG. 6B, the thus treated plate P was turned over to measure the load at the time when the bending angle again became 150°, and this step was repeated 20 times to measure retaining ratio of the bending strength. Results of the measurement of the plate cut out in the direction of 0° was shown in the graph of FIG. 7, results of the measurement of the plate cut out in the direction of 45° was shown in the graph of FIG. 8 and results of the measurement of the plate cut out in the direction of 90° was shown in the graph of FIG. 9.

COMPARATIVE EXAMPLE 1

For the sake of comparison, the prismatic billet obtained in Example 1 was heated at 110° C. and uniaxially drawn at a draw ratio of 2.5. The thus drawn molding was cut out in a direction of 0°, 45° or 90° using the uniaxially drawn direction as 0°, thereby preparing a rectangular plate of 30 mm in length×5 mm in width×1.5 mm in thickness, and each plate was subjected to bending strength test and repeated bending strength test in the same manner as described in Example 1. Results of the bending strength test are shown in the following Table 1, and results of the repeated bending strength test are comparatively shown in the graph of FIG. 7 (cut out direction: 0°), the graph of FIG. 8 (cut out direction: 45°) and the graph of FIG. 9 (cut out direction: 90°).

TABLE 1

|  |  | Bending strength (MPa) | | |
|---|---|---|---|---|
|  |  | 0° | 45° | 90° |
| Example 1 | Multi-axially oriented compression molding of PLLA $\overline{Mv}$ = 250,000 (average) | 265 | 260 | 258 |
| Comparative Example 1 | Uniaxially drawn and oriented molding of PLLA $\overline{Mv}$ = 250,000 (average) | 220 | 213 | 205 |

As is evident from Table 1, all of the plates cut out in the cut out directions of 0°, 45° and 90° from the multi-axially oriented compression molding of Example 1 showed an initial bending strength of around 260 MPa which was higher than the bending strength of biological bone (200 MPa). Also, difference in the cut out direction does not cause significant difference in the bending strength, so that these plates have almost the same bending strength and do not show anisotropy in view of strength. On the other hand, the uniaxially drawn plates showed lower strength than the above, and anisotropy in view of strength was found.

Figure 7:
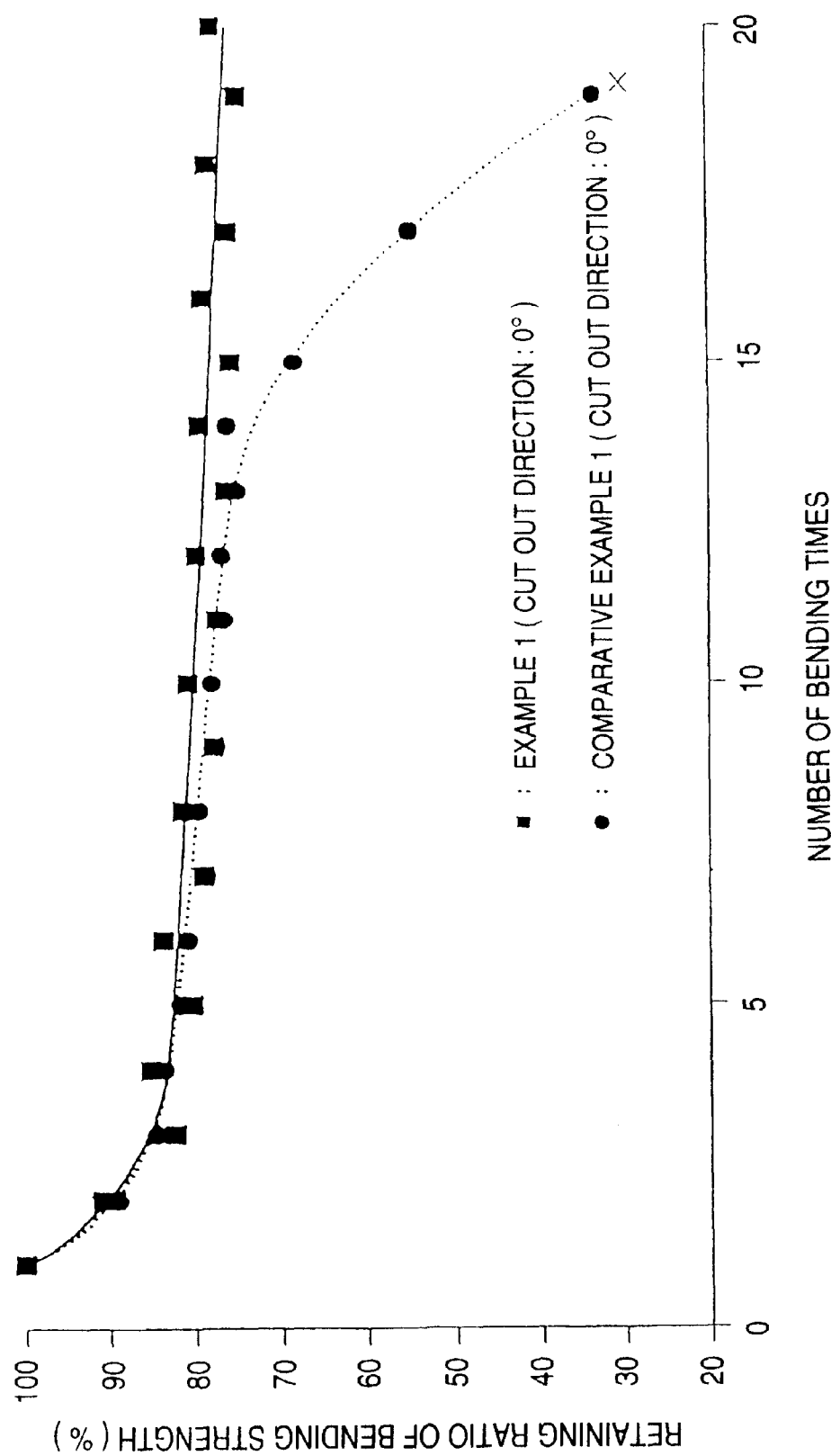
FIG. 7 is a graph showing a relationship between the number of times of bending deformation and the retaining ratio of bending strength, examined using a plate of Example 1 having a cut out direction of 0° and a plate of Comparative Example 1 having a cut out direction of 0°.
Figure 8:
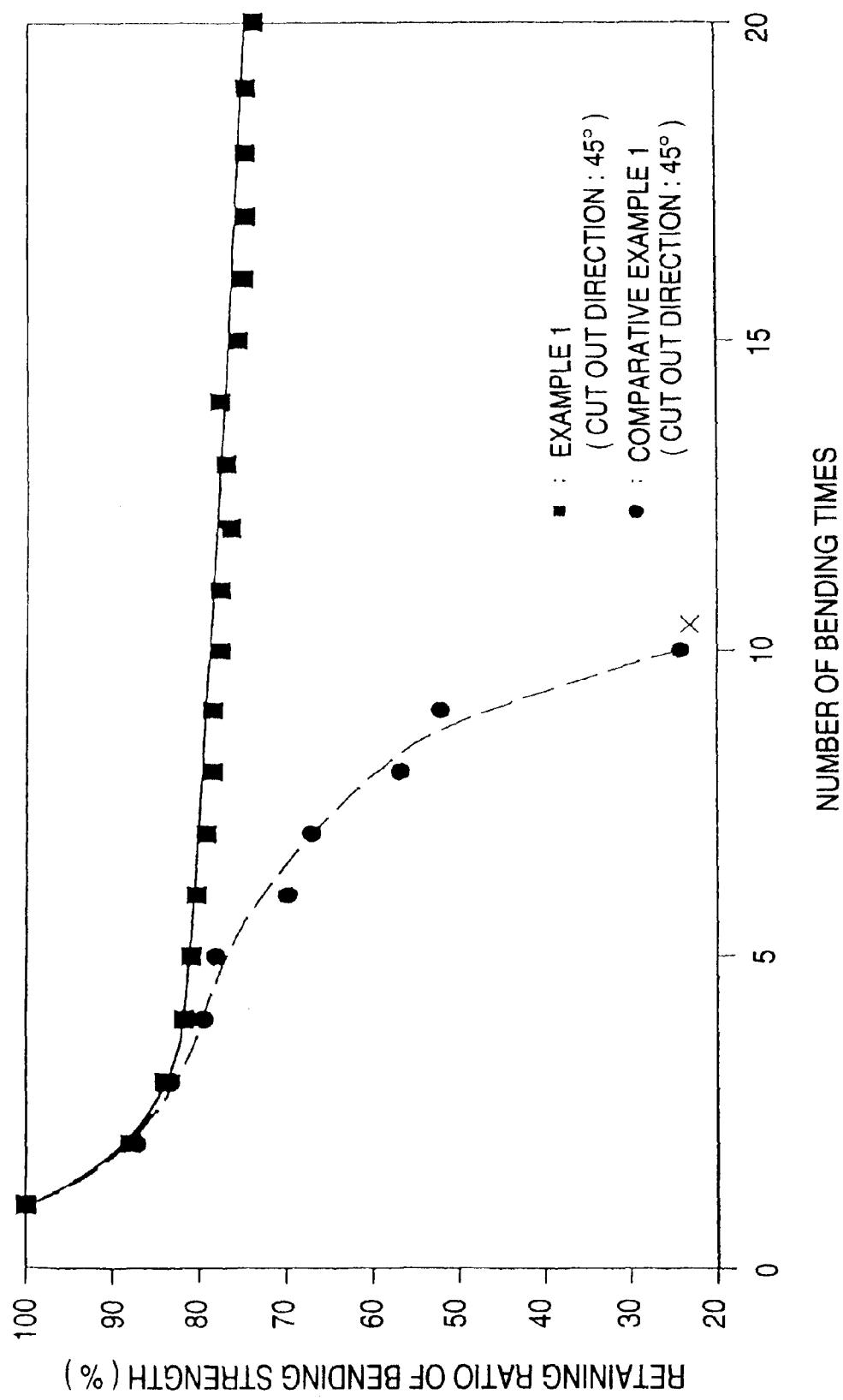
FIG. 8 is a graph showing a relationship between the number of times of bending deformation and the retaining ratio of bending strength, examined using a plate of Example 1 having a cut out direction of 45° and a plate of Comparative Example 1 having a cut out direction of 45°.
Figure 9:
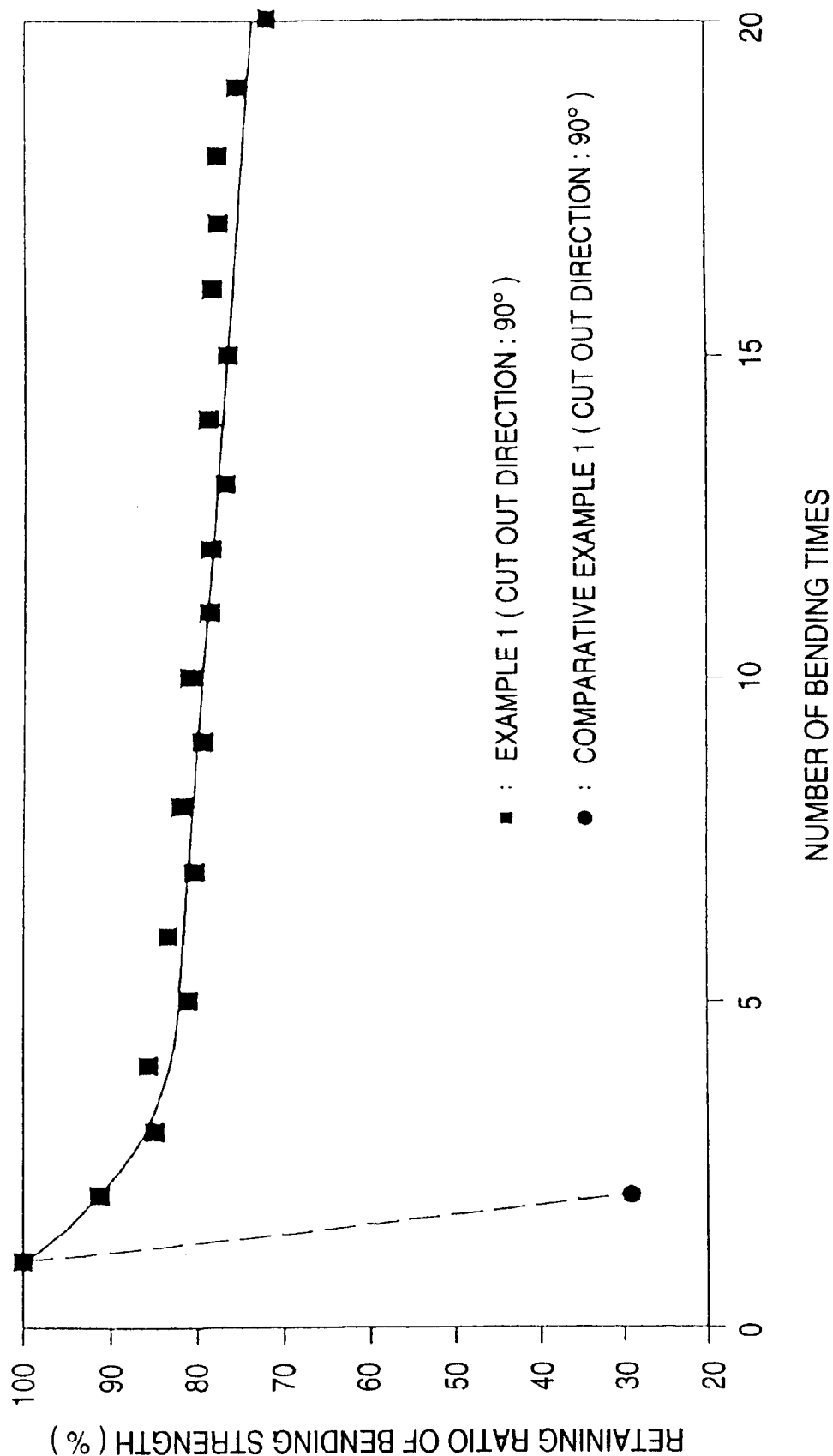
FIG. 9 is a graph showing a relationship between the number of times of bending deformation and the retaining ratio of bending strength, examined using a plate of Example 1 having a cut out direction of 90° and a plate of Comparative Example 1 having a cut out direction of 90°.

In addition, as is evident from the graphs of FIGS. 7 to 9, bending strength of the plate of Example 1 cut out in any direction decreased to 80% (212 MPa) of its initial bending strength by the 1st to 5th bending deformation caused by the residual distortion at the time of molding, but the residual distortion disappeared thereafter by the shape adjustment so that the strength was not substantially decreased and about 80% of the initial bending strength was maintained until 20th bending deformation, and breakage of the plate did not occur. It is evident from these results that each of the plates of Example 1 is a plate which maintains a strength higher than the bending strength of biological bone even against severe repeated bending deformation at room temperature (22° C.) and has toughness showing no anisotropy in view of the bending strength and its retaining ratio.

In the case of the plates of Comparative Example 1, on the contrary, anisotropy was observed in terms of bending strength and its retaining ratio by the repeated bending deformation, and the plate cut out at 0° maintained the strength most long but its bending strength decreased when the number of times of bending deformation exceeded 12 and reduced to about 35% of the initial bending strength by 19th bending deformation. On the other hand, the plate cut out in the direction of 45° showed rapid reduction of the strength retaining ratio when the number of bending deformation exceeded 5 times and was broken by fatigue by the 10th bending deformation. Also, the plate cut out in the direction of 90° was broken by the 2nd bending deformation. Accordingly, the plate oriented by uniaxial drawing was a plate having no toughness, which showed not only low initial bending strength but also significant anisotropy in view of the retaining ratio of strength by repeated bending deformation.

In this connection, deformation restoration was not observed when a plate deformed at ordinary temperature (particularly a plate bent at a room temperature of 37° C. or less) was soaked in hot water of 37° C. for 10 days or more.

EXAMPLE 2

Using granules of PLLA having a viscosity average molecular weight of 250,000 in which 40% by weight of un-sintered and un-calcined hydroxyapatite (u-HA) was uniformly dispersed, a plate-shaped multi-axially oriented compression molding having a viscosity average molecular weight of 160,000 containing u-HA was obtained in the same manner as described in Example 1. The thus obtained multi-axially oriented compression molding was subjected to cutting processing to cut out in a direction of 0°, 45° or 90° in the same manner as described in Example 1, thereby preparing a rectangular plate of 30 mm in length×5 mm in width×1.5 mm in thickness, and each plate was subjected to bending strength test and repeated bending strength test in the same manner as described in Example 1.

As the results, the initial bending strength of the plate cut out in the direction of 0° was 268 MPa, that of the plate cut out in the direction of 450 was 266 MPa and that of the plate cut out in the direction of 90° was 262 MPa, each of which showing higher bending strength than that of biological bone (200 MPa), and difference in the bending strength was hardly found by the cut out direction. In addition, due to the adjustment and disappearance of residual distortion, bending strength of the plate cut out in any direction was decreased to about 80% of its initial bending strength by the 1st to 5th bending deformation but was not substantially decreased thereafter, the strength retaining ratio was about 75% at the time of the 20th bending deformation, and breakage of the plate did not occur. It is evident from these results that each of the plates comprises a multi-axially oriented compression molding containing a bioceramics powder is also a plate which has toughness and does not show anisotropy in view of the bending strength and its retaining ratio. In this connection, deformation restoration was not found at 37° C.

EXAMPLE 3

In the same manner as described in Example 1, a prismatic billet of 250,000 in viscosity average molecular weight having a rectangular section of 10 mm in length×25 mm in width.

This billet was forged at 110° C. by press-charging it into the cavity of a forming mold of 5 mm in height×20 mm in width×300 mm in length, thereby obtaining a molding. This molding was again subjected to the forging molding by changing its mechanical direction (MD) to obtain a plate-shaped multi-axially orientated compression molding of 300 mm in length×45 mm in width×2.5 mm in thickness. A prism of 2.5 mm in height×2.5 mm in width×300 mm in length was prepared by cutting the plate-shaped molding, and a wire having a circular section of 1.5 mm φ was prepared by cutting corners of the prism.

Figure 10A:
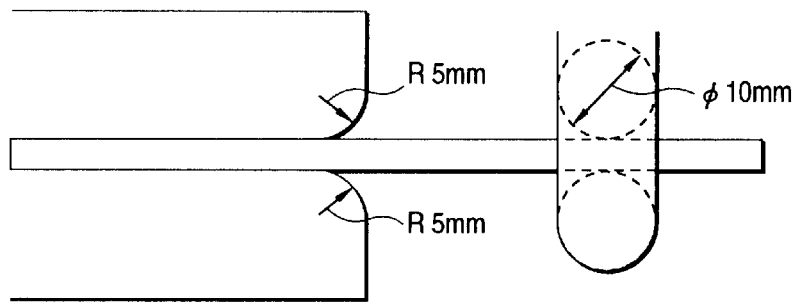
FIG. 10 is an explanatory drawing showing the repeated bending test of a wire carried out in Example 3, in which 10A shows a fixed condition of the wire, 10B shows a condition bent downward at 15° and 10C shows a condition upward at 15°.
Figure 10B:
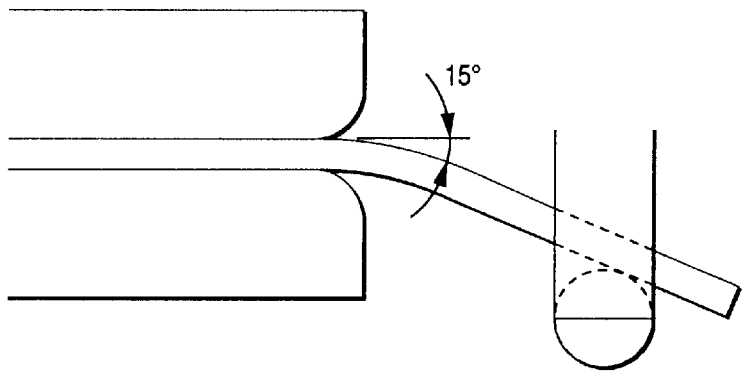
Figure 10C:
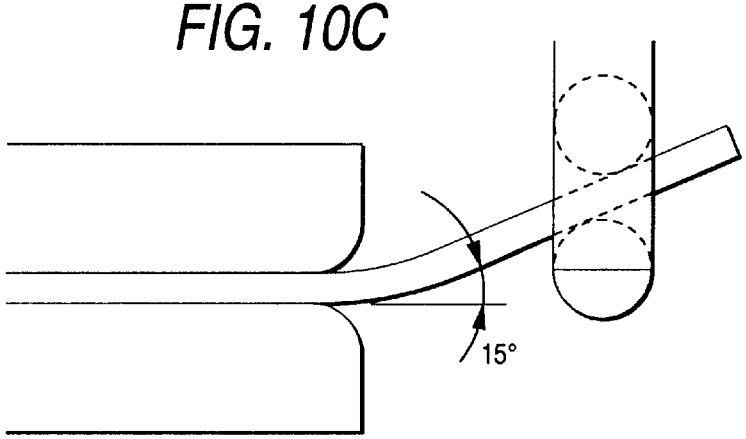

As shown in FIG. 10A, one end of the thus prepared wire was fixed with two metal plates, and the other end was fixed by holding it between two cylinders. As shown in FIG. 10B, this wire was bent until its bending angle became 15° against its central point, and the load at that time was measured. Also, as shown in FIG. 10C, this wire was again bent upward to measure the load at the time when the bending angle again became 15°, and this step was repeated 800 times to measure retaining ratio of the bending strength.

For the sake of comparison, a kirschner having a thickness of 1.5 mm φ was measured in the same manner. The results of measurement are shown in FIG. 11.

Figure 11:
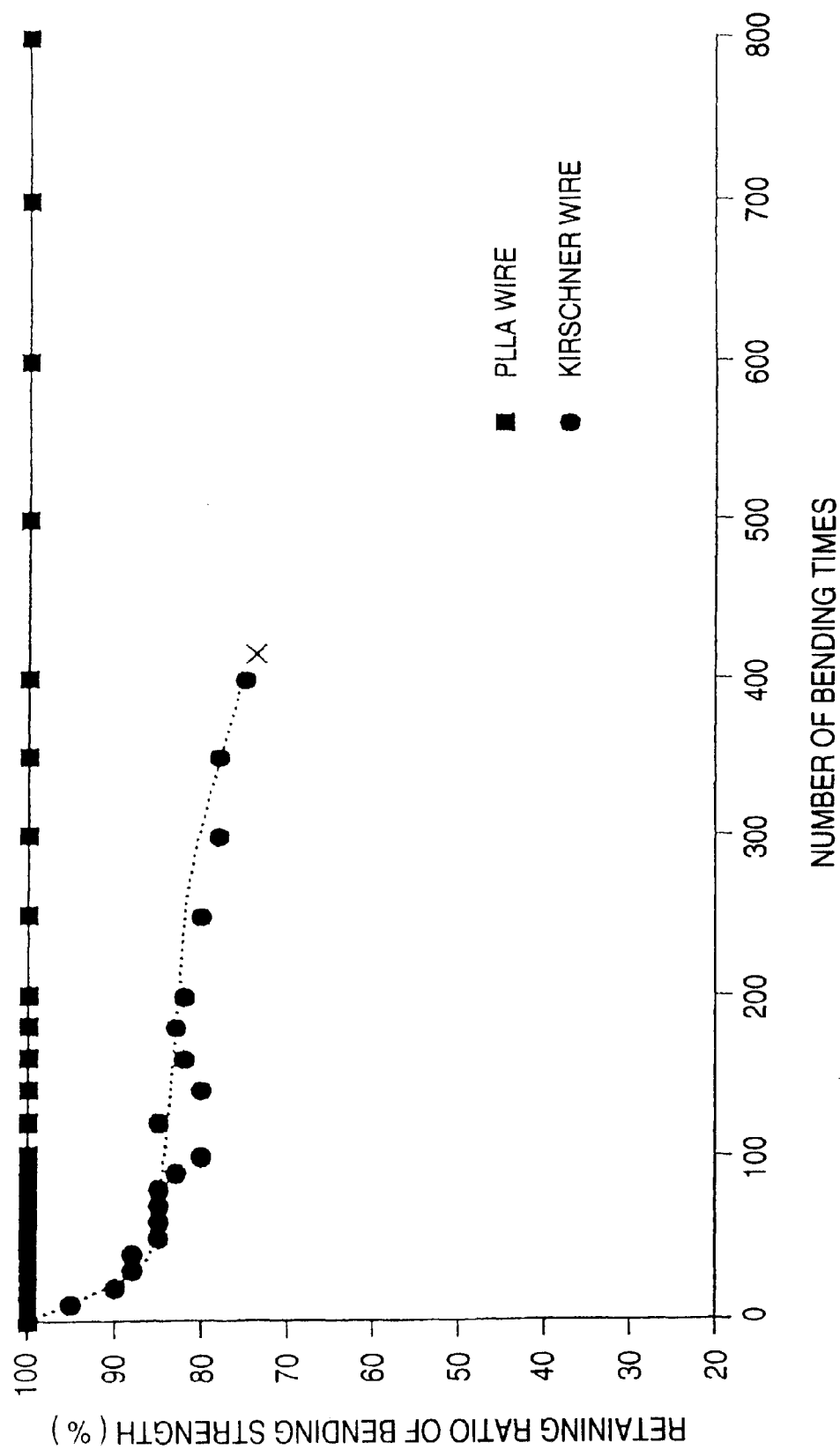
FIG. 11 is a graph showing a relationship between the number of times of bending deformation and the retaining ratio of bending strength, examined using a wire of Example 3 and a kirschner wire.

As is evident from FIG. 11, strength of the kirschner wire was decreased to 80% of its initial bending strength by the 50th bending deformation. Thereafter, decrease in the strength was not found until 200 to 300 times of bending deformation, but the strength was gradually decreased by 300 or more times of bending deformation, and the wire was broken by the 400th bending deformation.

On the contrary, the PLLA wire retained its initial bending strength by the 800th bending deformation and was not broken. Accordingly, it is evident that the PLLA wire is a wire having stronger toughness than the kirschner wire, which can retain its strength even against severe repeated bending deformation at room temperature (22° C.).

EXAMPLE 4

A wire having a diameter of 1 mm prepared as described above was bent until the bending angle became 90° downward or upward. One hundred X Ray photographs at the bent part were taken to analyze the change of microcrystalline orientation with extremely high accuracy.

With respect to the wire bent upward at 90°, about 65% of the microcrystals were slanted at 72.50, but about 20% of the microcrystals did not follow the orientation. The orientation was distributed from about 65° to about 80° and predominantly within the range of about 11.50. With respect to the wire bent downward at 90°, the similar tendency in the orientation was found in the direction of the bending, but the orientation was distributed in a wider range of about 22.5°. About 15% of the microcrystals were oriented in the direction of 30 upward.

The result shown above means that bending the wire at ordinary temperature causes the orientation direction change of the crystal chains oriented along many axes or clusters thereof, and the change occurs with a distribution. In other words, it was found that the microcrystalline distribution changes from a place to a place based on the stress relaxation accompanying the deformation by the outer force at ordinary temperature. Thus, it is considered that the orientation of microcrystals that followed the deformation supports the strength along with the direction of deformation and the orientation of crystals that remained intact supports the original strength before deformation.

EXAMPLE 5

Using the billet obtained in Example 1, a molding (plate) forged one time in the direction of MD1 and a molding (plate) further forged in the direction of TD direction (i.e., MD2) were prepared. The state of crystal orientation of these moldings were analyzed by the X ray diffraction method (analysis by the X ray transmission photography using a wide X ray flat camera). Several samples were layered to measure a wide range of intensity and about ten X ray photographs were taken for each of the place in order to achieve accurate analysis. The deformation ratio of the first and second forgings was 2.5, respectively. MD1 and MD2 forms an angle of 90°, i.e., in the relation of MD and TD. Representative photographs are shown as FIGS. 12A, 12B, 13A, and 13B.

Figure 12A:
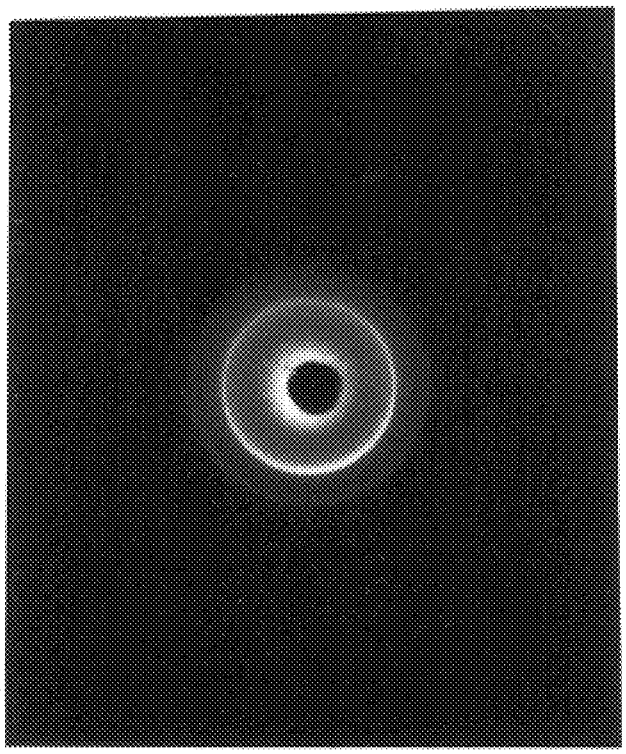
FIGS. 12A and 12B are X ray photographs of the molding forged one time.

FIG. 12A is an X ray photograph of the molding forged one time, when the incident angle of the X ray was parallel to the mechanical direction MD1. In this photograph, the diffraction of axis a and axis b draws a circle but the intensity is not symmetric about the meridian (confirmed by the measurement using a slanted sample), which indicates that the orientation of paracrystals was slanted at an angle of 10° toward the operation axis. In this regard, the angle of the tapered part of the forming mold for the forging was 15°.

Figure 12B:
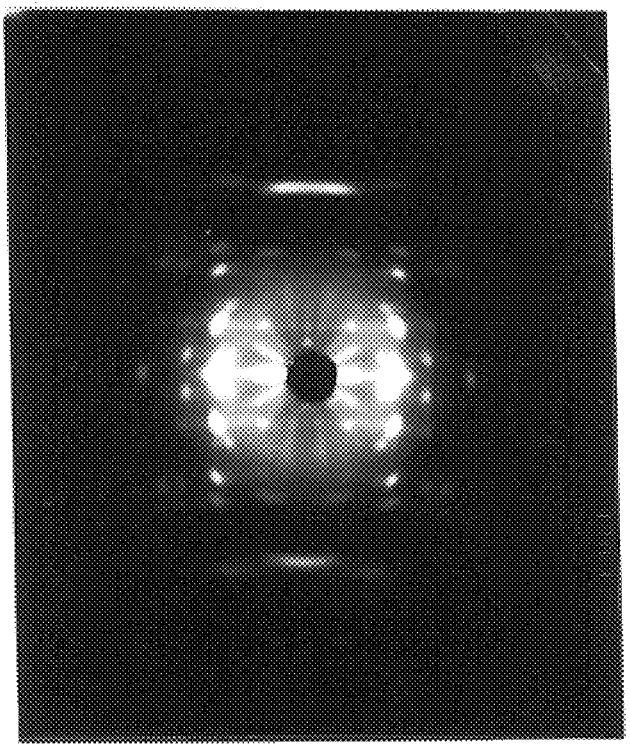

FIG. 12B is an X ray photograph of the molding forged one time, when the incident angle of the X ray was right to the mechanical direction MD1. The photograph shows developed layered lines and remarkable spots appeared asymmetrically about the equator. The results support that the molecular chains were slanted toward the operation axis.

Figure 13A:
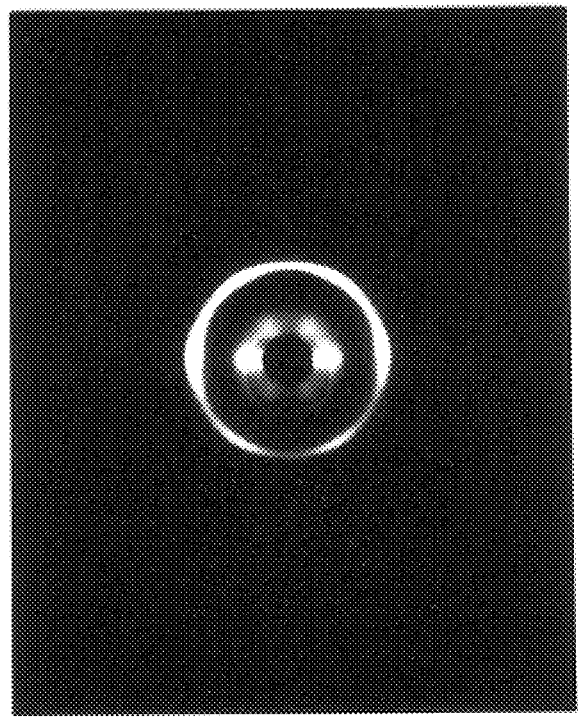
FIGS. 13A and 13B are X ray photographs of the molding forged two times according to the present invention.
Figure 13B:
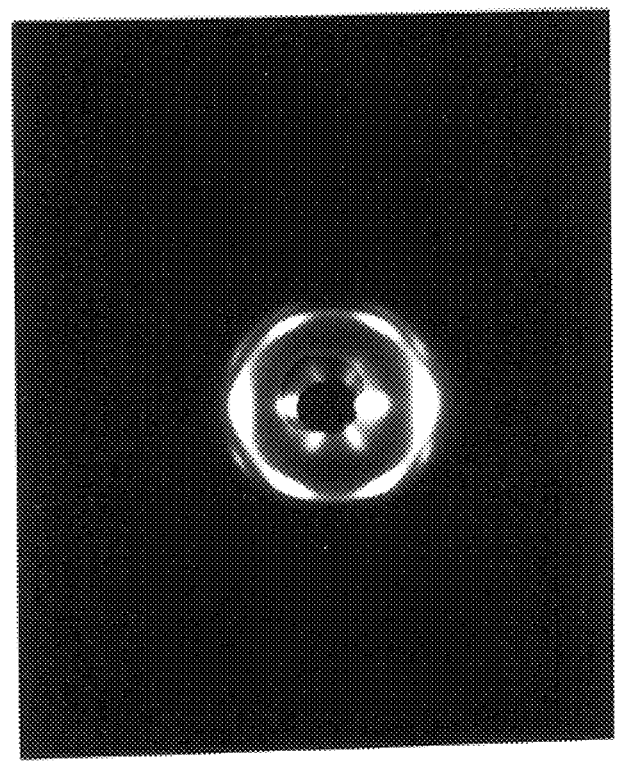

FIG. 13A is an X ray photograph of the molding forged two times according to the present invention, when the incident angle of the X ray was parallel to the mechanical direction MD2 (i.e., right to the plate surface). FIG. 13B is an X ray photograph of the molding forged two times according to the present invention, when the incident angle of the X ray was right to the mechanical direction MD2 (i.e., parallel to the plate surface). As is understood from these results, a part layered in the thickness direction was found at the center part of the plate. These photographs in combination indicate that molecular chains were oriented with many reference axes and state of crystals was considerably irregular.

Figure 14:
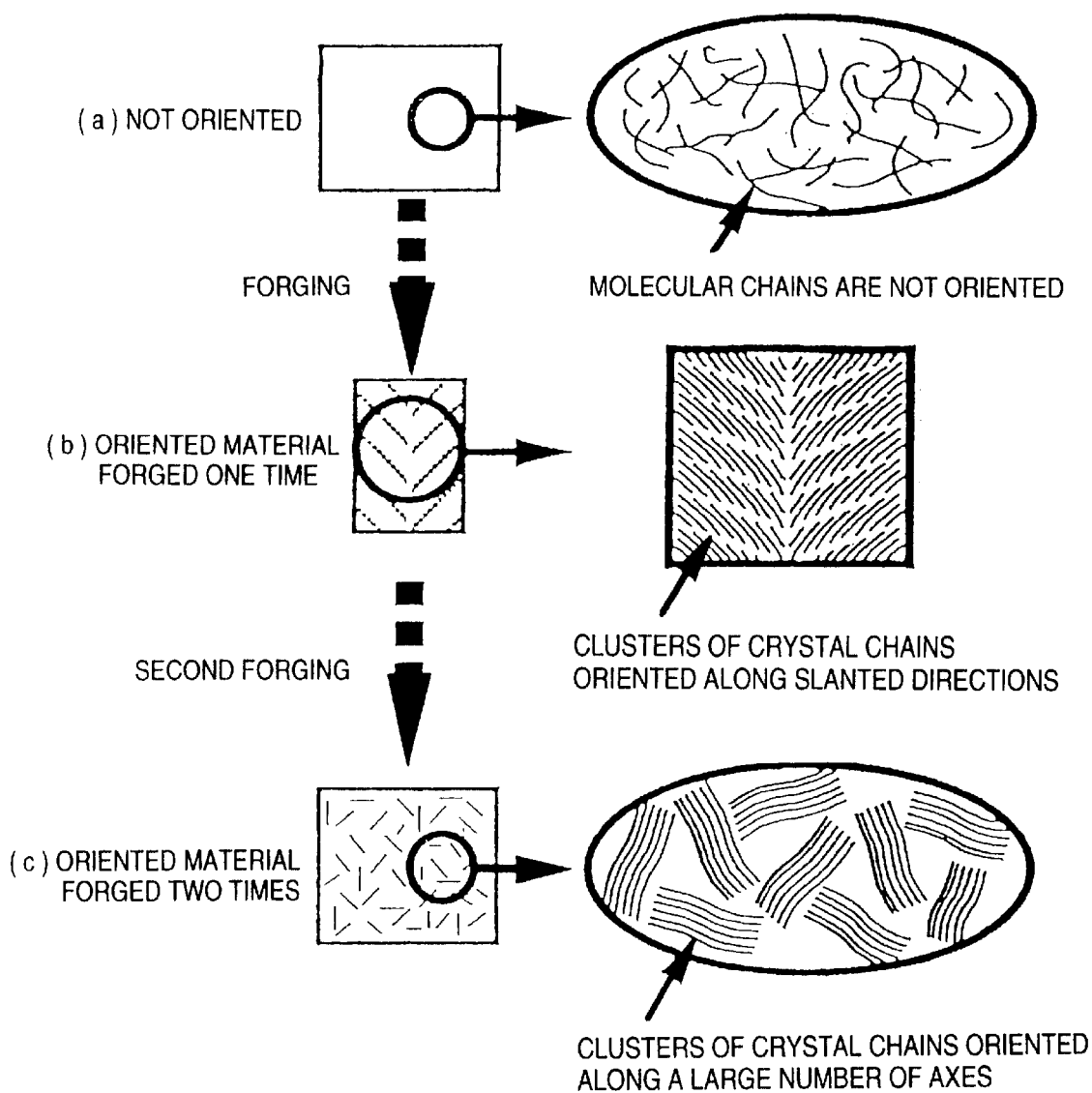
FIG. 14 is a drawing explaining the morphological change of the orientation.

From the above results, it was confirmed that the crystals oriented with a slant of about 10° toward MD after the first forging changed to have an assembled morphology having many reference axes by the second forging. FIG. 14 shows the process of the formation and morphological change of the orientation. As a result, it was suggested that this morphology is the scientific reason why the material of the present invention shows strength in the various directions against deformation.

Thus, as has been described in the foregoing, the biodegradable and bioabsorbable implant device of the present invention exerts many remarkable effects, for example, because it has high mechanical strength and its shape after deformation such as bending and twisting within ordinary temperature range can be fixed and maintained, its shape can be easily adjusted at the site of operation, since it has substantially no anisotropy in view of strength, it does not cause whitening, breakage and sharp decrease in strength (deterioration) when its bending deformation is repeated in any direction and it has toughness, and the implant material for osteosynthesis use which contains a bioceramics powder can bind to bones and fix the fractured bone parts without loosening within a short period of time.

In addition, the shape-adjusting method of the present invention is a method by which shapes of the implant material can be easily adjusted due to the employment of a means that overturns common knowledge on the deformation of plastics, namely a means to carry out bending deformation and torsional deformation within ordinary temperature range, so that the troublesome prior art deformation by heating at a high temperature can be avoided.

While the invention has been described in detail and with reference to specific embodiments thereof, it will be apparent to one skilled in the art that various changes and modifications can be made therein without departing from the spirit and scope thereof.

This application is based on Japanese patent application No. Hei.-10-279389 filed on Sep. 14, 1998, incorporated herein by reference.

What is claimed is:

1. A biodegradable and bioabsorbable implant material which comprises a biodegradable and bioabsorbable crystalline polymer capable of effecting deformation within ordinary temperature range and having a shape-keeping ability to fix and maintain the shape after deformation as such, wherein molecular chains, domains of molecular chain assembly or crystals of the biodegradable and bioabsorbable polymer are multi-axially oriented along three-dimensionally oriented reference axes having different axial directions, or clusters having these reference axes having different orientation are assembled.

2. The biodegradable and bioabsorbable implant material according to claim 1, wherein it is obtained by forging a billet comprising a biodegradable and bioabsorbable crystalline polymer at a low temperature and then forging the same at a low temperature by changing its mechanical direction.

3. The biodegradable and bioabsorbable implant material according to claim 1, wherein the biodegradable and bioabsorbable crystalline polymer is a crystalline polylactic acid.

4. The biodegradable and bioabsorbable implant material according to claim 1, wherein it is formed into a flat heteromorphic shape.

5. The biodegradable and bioabsorbable implant material according to claim 1, wherein it is formed into a cylindrical shape.

6. The biodegradable and bioabsorbable implant material according to claim 1, wherein it further comprises a bioceramics powder.

7. The biodegradable and bioabsorbable implant material according to claim 1, wherein the state of orientation of molecular chains, domains of molecular chain assembly or crystals of the biodegradable and bioabsorbable polymer partially changes by the deformation within ordinary temperature.

8. A method for adjusting shape of a biodegradable and bioabsorbable implant material, which comprises effecting bending deformation and/or torsional deformation of the biodegradable and bioabsorbable implant material as set forth in any one of claims 1 to 7 within ordinary temperature range.

9. The biodegradable and bioabsorbable implant material according to claim 4, wherein the flat heteromorphic shape is a sheet, a plate, a plate having screw-inserting hole(s), a washer, a button, a mesh or a ribbon.

10. The biodegradable and bioabsorbable implant material according to claim 5, wherein the cylindrical shape is a wire, a cable, a rod or a pin.

* * * * *